United States Patent [19]

Stein, III

[11] Patent Number: 5,201,210
[45] Date of Patent: Apr. 13, 1993

[54] NEEDLE BENDING DEVICE

[76] Inventor: William Stein, III, 4701 Richland Ave., Metairie, La. 70002

[21] Appl. No.: 791,027

[22] Filed: Nov. 12, 1991

[51] Int. Cl.$^5$ ............................................. B21D 7/022
[52] U.S. Cl. ....................................... 72/457; 72/479; 140/123; 140/147
[58] Field of Search ............... 140/123, 147, 105, 106; 72/457, 458, 479

[56] References Cited

U.S. PATENT DOCUMENTS

| | | | |
|---|---|---|---|
| 907,210 | 12/1908 | Williams | 72/457 |
| 1,578,462 | 3/1926 | Myers | 72/457 |
| 2,498,114 | 2/1950 | Penrod | 72/479 |
| 2,824,474 | 2/1958 | Lawrence | 72/458 |
| 2,824,475 | 2/1958 | Rolando | 140/123 |
| 2,990,734 | 7/1961 | Jackson | 72/479 |
| 3,700,011 | 10/1972 | Walter | 140/147 |
| 4,421,145 | 12/1983 | Broberg, Jr. | 140/123 |

Primary Examiner—David Jones
Attorney, Agent, or Firm—Stephen R. Doody

[57] ABSTRACT

A needle bending device for bending a needle to any desired length without damaging the lumen of the needle and while maintaining sterile conditions, comprise a plastic casing having an open aperture and elongated chamber. The chamber is maintained sterile and the aperture is provided with a curved crown so that the needle can be bent around the crown. Graduated markings on the outer surface of the casing can be used in conjunction with transparent material for the casing, to see the length of needle within the casing and provide a bend of suitable length. Bends having angles of 90°, more than 90° or less than 90° can also be provided by bending the needle to any desired extent around the curved crown.

11 Claims, 2 Drawing Sheets

NEEDLE BENDING DEVICE

FIELD AND BACKGROUND OF THE INVENTION

The present invention is in the field of needles and hypodermic syringes. More particularly, the present invention is directed to a device that is capable of receiving and bending needles to desired lengths and angles.

It is very common in the medical field of intravenous therapy or intravenous vesicant drug treatment, to use a device for allowing frequent, atraumatic and relatively simple access to a patient's veins. One such device is shown in FIG. 8 and includes an intravenous catheter 110 that is inserted beneath the skin 112 along with a port chamber or reservoir 114. Chamber 114 includes an upper septum material 122 and is enclosed by a casing 124.

A special "non-curing" needle 116 is used in conjunction with the chamber and intravenous catheter. The needle is inserted through the patient's skin into chamber 114 and left for varying periods of time in order to meet intravenous drug treatment demands as required. Needle 116 has a hollow shaft 118 which ends at an inclined closed end 117. A side hole 119 allows the drug to pass out of the needle lumen and into chamber 114, and prevents coring of septum 122 by the needle.

Because the needle must be left in a patient for prolonged periods of time, it is standard practice to secure the needle hub 120 and shaft 118 to the patient's skin. The optimum configuration for such a needle is to bend it at a 90° angle which allows the needle to pass through the skin and be aligned in a perpendicular arrangement with the port chamber. This configuration allows the exposed portion of the needle, including the hub, to lie parallel to the skin.

Having the exposed needle portion arranged in this manner decreases incidence of infection, secures the needle so that it is not inadvertently dislodged and prevents unnecessary movement of the needle, alleviating undue wear of the septum material 122 in the chamber 114, which can result in premature failure of the septum material.

The special preformed needles required for this type of intravenous treatment are supplied either straight or with a right angle bend. Because the straight needles are difficult to secure to a patient, they are seldom used in this application. Additionally, the needles preformed at a right angle bend also pose a problem. Because the needles are preformed at right angles, the inserted portion of the needle, i.e., the portion of the needle that extends from the tip to the right angle bend, is seldom of a proper length to ensure that the needle is secured firmly and properly in the patient during the intravenous drug therapy.

Because the preformed, right angle bend needles are mass produced for medical use, many patients are not afforded a firm securing of the needle that is most efficient. In order to achieve a result where each patient has the most secure fit of the inserted needle, each needle must vary accordingly in the portion of the needle that is inserted beneath the skin, that is the length of the needle extending from the tip to the right angle bend.

The present invention is designed to solve or substantially ameliorate the above-described problems.

SUMMARY OF THE INVENTION

It is an object of the present invention to provide a needle bending device which allows a needle to be bent so that the length of the inserted portion of the needle is at a length that achieves the best possible attachment and must secure fit for each individual patient.

It is another object of the present invention to eliminate the need to stock pre-bent needles that cannot be adopted for the most efficient fit on a case-by-case basis.

It is also an object of the invention to allow the needle to be bent by the user grasping the device while still provided a sterile environment for the needle.

It is a further object of the invention that the needle can be bent without damaging the needle tip or lumen, or inadvertently injuring the user.

The foregoing and other objects and advantages are attained by a needle bending device that can be made of a material such as injection-molded plastic, intended as a single use, disposable item, or as an item that can be easily sterilized by steam or gas for re-use, having a casing or sheath that is molded such that a needle can be inserted through the opening of the casing. The casing can have a flat surface area and be partly or entirely made of a transparent material. The flat area has graduated marks positioned at predetermined intervals so that, as the needle is inserted into the casing, the position of the bend in the needle at a desired insertion length, can be determined depending on each patient's unique individual needs. Because the casing has a crown that is curved outwardly, the needle can be bent by conforming the needle over the curved surface to prevent any problem of a "kinking" or uneven bending. The needle can thus be bent without damage to its lumen or danger of breaking of the needle.

The features of the present invention can be best understood together with further objects and advantages thereof, by reference to the following description, taken in connection with the accompanying drawings, wherein like numerals indicate like parts.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
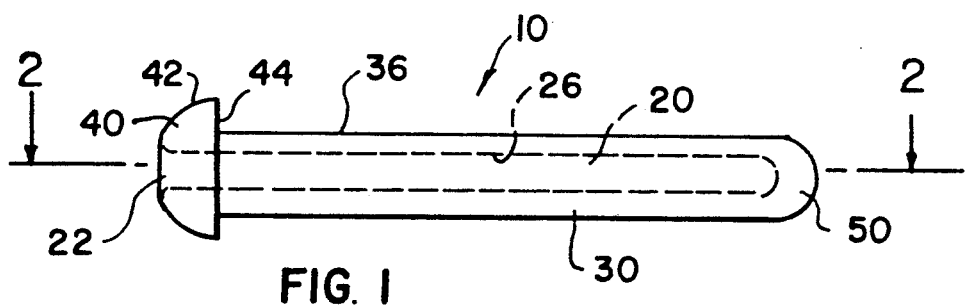
FIG. 1 is a side elevational view of a needle bending device according to the present invention.

Referring to FIG. 1 in particular, the invention embodied therein comprises a needle bending device generally designated 10 for use in the medical field. The device 10 comprises a casing 30 constructed from a material such as injection molded plastic. The casing 30 extends to a rear end 50 and has a crown 40 located opposite the rear end 50. The crown 40 is positioned perpendicularly to the casing 30 and has a crown edge 42 curved outwardly in a curved or circular form. A crown base 44 forms an under side for the crown 40. An aperture 22 is located in the center of the crown 40 and is at the beginning of a chamber 20 which extends longitudinally within the casing 30. The chamber 20 is circular in cross-section and has a chamber wall 26 that extends from the crown 40 to the closed chamber end 50.

The chamber 20 is shaped to hold a needle 21 in the aperture 22. Once the needle is inserted within the confines of the chamber 20, the user can easily bend the needle to a desired configuration or angle by applying pressure to the portion of the needle remaining outside the device 10, against the crown 40. By conforming the exposed needle portion to the contour of the crown edge 42, the user can bend the needle to a desired angle. Throughout the bending process, the needle should rest firmly within the chamber 20 with the assistance of the chamber wall 26.

Figure 2:
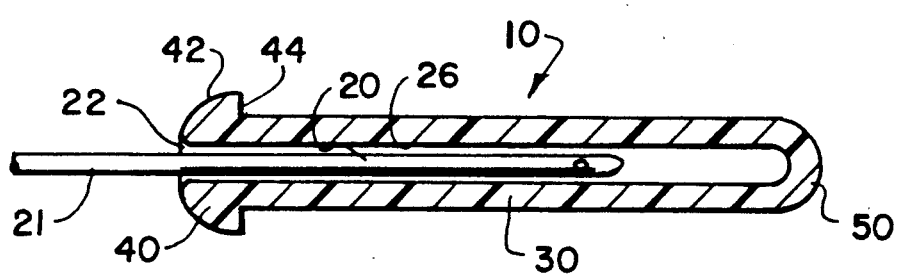
FIG. 2 is a longitudinal, sectional view of the needle bending device according to the present invention, taken along line 2—2 of FIG. 1 and showing a non-coring needle to be bent therewith.
Figure 3:
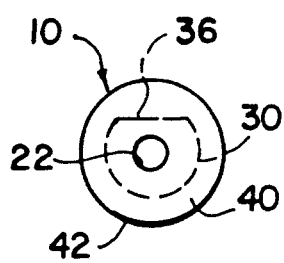
FIG. 3 is a front end view of the needle bending device of FIG. 1.
Figure 4:
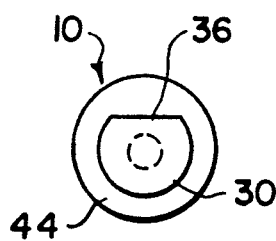
FIG. 4 is a rear end view of the needle bending device of FIG. 1.

As shown in FIGS. 2 and 4, the casing 30 is largely circular except for an outer casing side wall 36 which has a flat surface that extends from the crown 40 longitudinally to the rear end 50.

Figure 5:
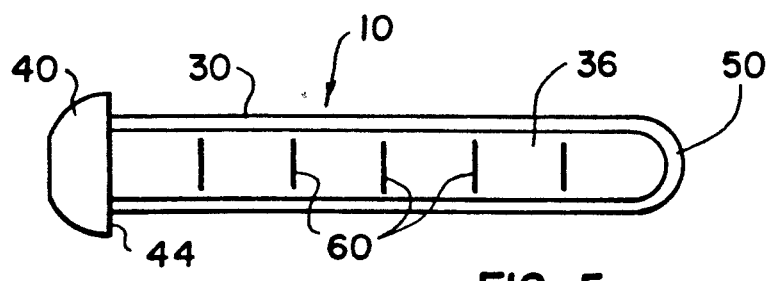
FIG. 5 is a top plan view of the needle bending device of FIG. 1.

The outer casing wall 36, as shown in FIG. 5, has graduated marks 60 depicted thereon so that the user can insert the needle into the device 10 through the aperture 22 to a marked extent, for bending against the crown 40 in order to achieve the desired bend in the needle. The marking 60 are typically 0.25 inches apart.

Figure 6:
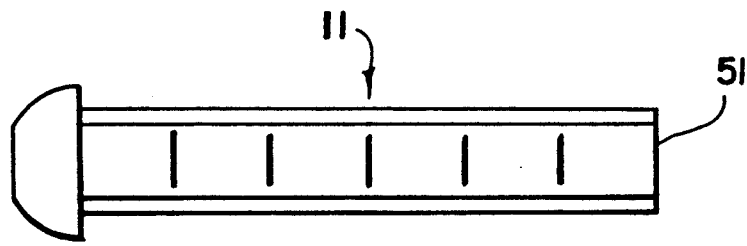
FIG. 6 is a view similar to FIG. 5 showing another embodiment of the needle bending device.

FIG. 6 illustrates a further embodiment of the invention in the form of a device generally designated 11 which is substantially the same as device 10, but which has a flat rear end 51 which is either open or closed. The closed end 50 shown in FIG. 5 is preferred, however, to maintain a sanitary protected area for the needle tip within the casing.

Figure 7:
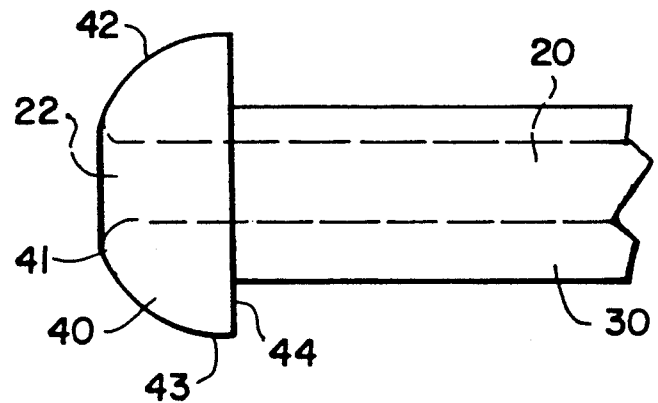
FIG. 7 is a partial enlarged side view of the device at its front end.
Figure 8:
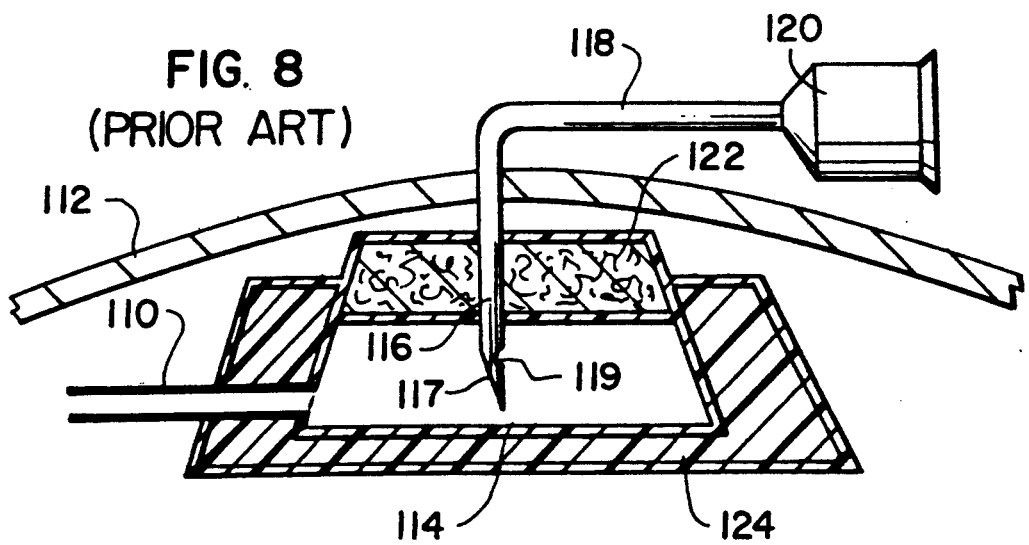
FIG. 8 is a schematic sectional view of an injection site with a non-coring needle bent according to the prior art.

FIG. 7 shows the crown 40 to have an inner portion 41 which is immediately adjacent the aperture 22 and which has a small radius of curvature of approximately 0.03 inches or a range of from 0.01 to 0.05 inches. The outer curved portion 43 of crown 40 has a large radius of curvature of approximately 0.2 inches or a range of 0.1 to 0.3 inches.

The inside diameter of chamber 20 is advantageously about 0.1 inches or within the range of 0.05 to 0.2 inches. Although the chamber diameter should be the same for all casings, it may be useful to provide smaller diameter chambers for needles having smaller gauges, and large diameter chambers for needles with large diameters.

The length of chamber 20 is from about 1 inch to about 2 inches long and preferable 1.5 inches long.

The maximum outside diameter of crown 40 is approximately 0.375 and within the range of 0.2 to 0.5 inches. It is useful to provide the crown 40 with a small radius of curvature inner portion 41 and a larger radius of curvature outer portion 43, to avoid kinking or damage to the lumen of the needle, and also to facilitate bend of greater than 90°, or conversely less than 90°, if desirable for a particular patient.

Casings 10 or 11 are made of any suitable material, preferably synthetic plastic material, which may be entirely or partially transparent, translucent or opaque.

While specific embodiments of the invention has been shown and described in detail to illustrate the application of the principles of the invention, it will be understood that the invention may be embodied otherwise without departing from such principles.

What is claimed is:

1. An injection needle bending device comprising:
   a sterile casing defining an elongated chamber with a rear end section and an open front end section opposite from the rear end section, the chamber being adapted to receive a length of injection needle into the open front end section and along at least part of the chamber;
   a crown that is curved outwardly from the open front end section and is arranged perpendicularly to the casing and positioned at the front end section of the casing, so that the injection needle can be bent over the crown to form a bent length of injection needle extending along the chamber to any desired extent, and in a sterile environment; and
   wherein the casing is made at least partly of a transparent material, and gradation means extending along the casing and visible with a length of needle extending in the chamber for providing a measurement of the length of the needle extending in the chamber.

2. An injection needle bending device comprising:
   a sterile casing made at least partly of a transparent material and defining an elongated chamber with a rear end section and an open front end section opposite from the rear end section, the chamber being adapted to receive a length of injection needle into the open front end section and along at least part of the chamber;
   gradation means extending along the casing and visible with a length of needle extending in the chamber for providing a measurement of the length of the needle extending in the chamber; and
   a crown that is curved outwardly from the open front end section and is arranged perpendicularly to the casing and positioned at the front end section of the casing, so that the injection needle can be bent over the crown to form a bent length of injection needle extending along the chamber to any desired extent, and in a sterile environment.

3. A needle bending device according to claim 2, wherein the casing has a flat outer side wall, said gradation means comprising a plurality of graded markings extending along the flat outer side wall.

4. A needle bending device according to claim 3, wherein the gradation markings are at intervals of about 0.25 inches.

5. An injection needle bending device comprising:
   a sterile casing defining an elongated chamber with a rear end section and an open front end section opposite from the rear end section, the chamber being adapted to receive a length of injection needle into the open front end section and along at least part of the chamber;

a crown that is curved outwardly from the open front end section and is arranged perpendicularly to the casing and positioned at the front end section of the casing, so that the injection needle can be bent over the crown to form a bent length of injection needle extending along the chamber to any desired extent, and in a sterile environment;

the rear end section of the casing being closed, the open front end section of the casing having a circular aperture with the crown curving outwardly from the aperture, the curvature of the crown having a radius of curvature that increases at least once from the aperture outwardly to an outer periphery of the crown.

6. A needle bending device according to claim 5, wherein the casing has a flat outer side wall and is made at least partly of a transparent material at the flat outer side wall so that a length of needle extending into the chamber is visible.

7. A needle bending device according to claim 5, wherein the casing is made at least partly of a transparent material, and gradation means extending along the casing and visible with a length of needle extending into the chamber for providing a measurement of the length of the needle extending into the chamber.

8. A needle bending device accordingly to claim 7, wherein the casing has a flat outer side wall, said gradation means comprising a plurality of gradated markings extending along the flat outer side wall.

9. A needle bending device according to claim 8, wherein the chamber has the length of from about 1 to about 2 inches.

10. A needle bending device according to claim 9, when the chamber has an inside diameter of from about 0.05 to about 0.2 inches.

11. A needle bending device according to claim 10, wherein the radius of curvature of the crown adjacent the aperture is about 0.01 to about 0.05 inches near the aperture.

* * * * *